United States Patent [19]

Ramsay et al.

[11] Patent Number: 5,980,246
[45] Date of Patent: Nov. 9, 1999

[54] ORTHODONTICS HEADGEAR COMPLIANCE MONITOR

[75] Inventors: Douglas S. Ramsay; Mani Soma; Chris Prall; George A. Barrett, all of Seattle, Wash.

[73] Assignee: The University of Washington, Seattle, Wash.

[21] Appl. No.: 09/043,659
[22] PCT Filed: Sep. 27, 1996
[86] PCT No.: PCT/US96/15533
  § 371 Date: Mar. 24, 1998
  § 102(e) Date: Mar. 24, 1998
[87] PCT Pub. No.: WO97/12299
  PCT Pub. Date: Apr. 3, 1997

Related U.S. Application Data

[60] Provisional application No. 60/004,382, Sep. 27, 1995.
[51] Int. Cl.$^6$ ...................................................... G04F 7/00
[52] U.S. Cl. ................................................................ 433/5
[58] Field of Search .............................. 433/2.5; 340/573

[56] References Cited

U.S. PATENT DOCUMENTS 3,885,310  5/1975  Northcutt .
4,226,589 10/1980  Klein ............................................. 433/5
4,255,138  3/1981  Frohn ........................................... 433/6
4,764,111  8/1988  Knierim ........................................ 433/5
4,846,157  7/1989  Sears .......................................... 178/36
5,651,671  7/1997  Seay et al. .................................... 433/5

Primary Examiner—Ralph A. Lewis
Attorney, Agent, or Firm—Frost & Jacobs LLP

[57] ABSTRACT

This invention is an apparatus and method for monitoring and motivating user compliance for orthodontic headgear (24) of the type using a linear spring force module (22). The spring force module (22) includes first (38) and second opposite attachment members that are interconnected to provide spring tension when moved linearly apart. A position sensor (16)(18)(19) detects liner movement between the attachment members. A microprocessor (12) receives signals from the position sensor to determine wear duration, force magnitude, and whether such movement is sufficiently variable to be biological in origin or is attempted mimicry. Multiple determinations made by the processor are recorded over time to provide an evaluation of headgear wear compliance and to provide ongoing motivation for user compliance.

20 Claims, 5 Drawing Sheets

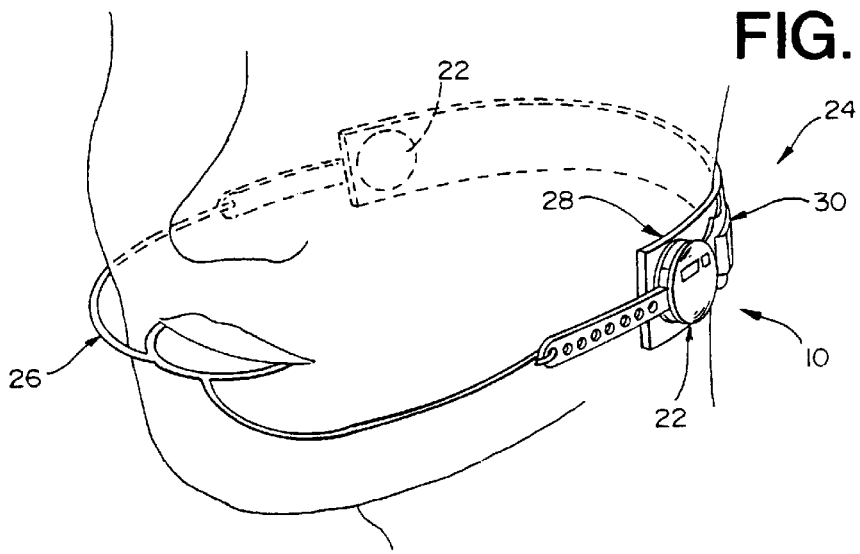
FIG. 1
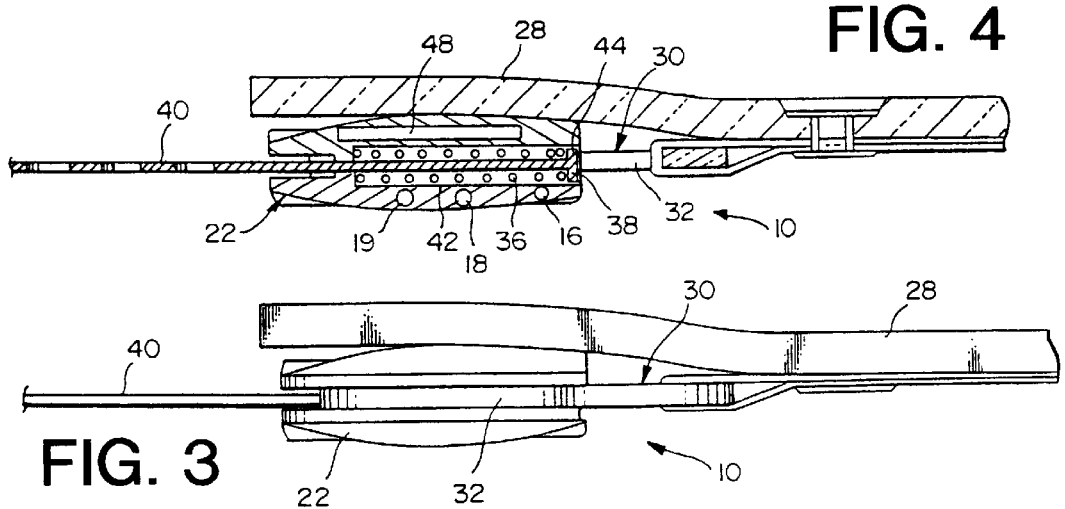
FIG. 4
FIG. 3
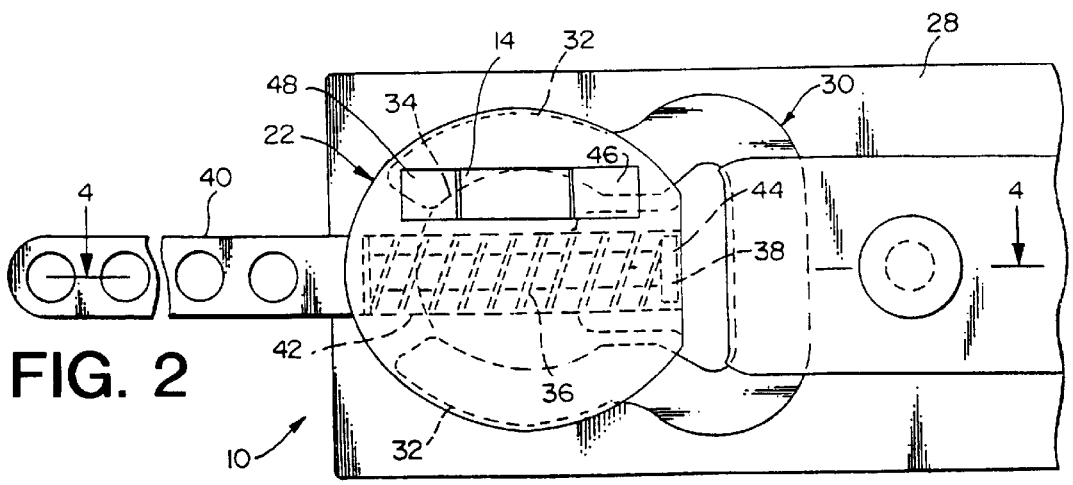
FIG. 2

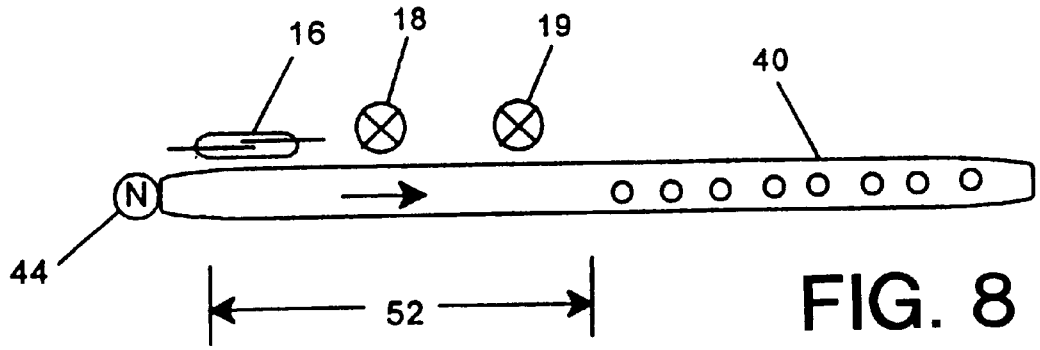
FIG. 8
FIG. 9
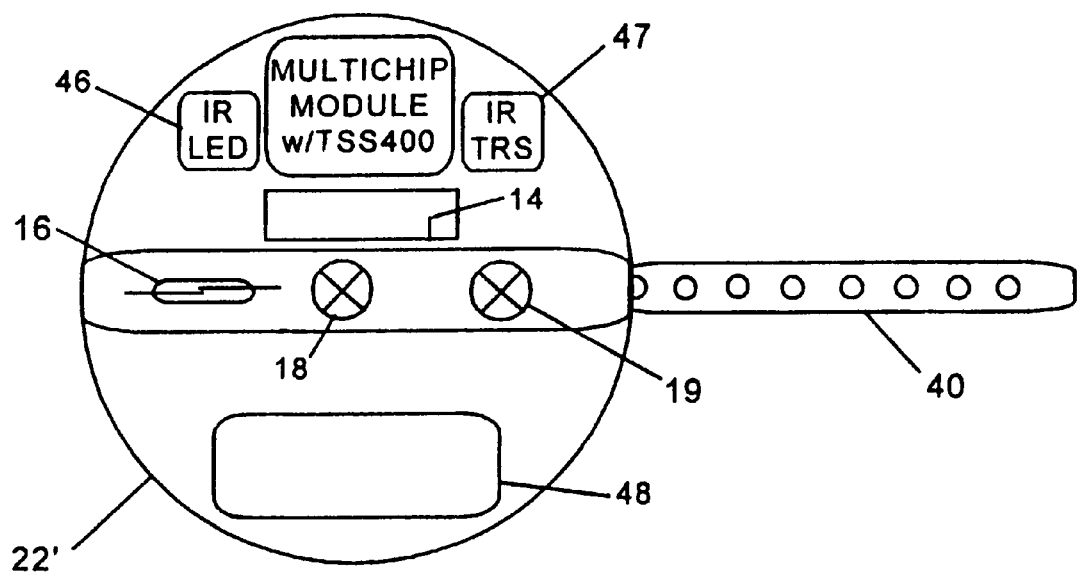

ORTHODONTICS HEADGEAR COMPLIANCE MONITOR

RELATED APPLICATION

This application was first filed as a provisional application on Sep. 27, 1995, Ser. No. 60/004,382, entitled, "Orthodontics Headgear Compliance Monitor."

TECHNICAL FIELD

This application describes an electronic device that will both measure and enhance the compliance of young orthodontic patients with wearing an orthodontic headgear which is a common removable orthodontic appliance. Furthermore, this device will measure the duration and amount of force applied during headgear use which is information of clinical and scientific importance.

BACKGROUND

There are approximately 8,856 orthodontic specialists in the United States, as well as an unknown number of dentists who provide orthodontic services. A survey of the members of the American Association of Orthodontists (more than 90% of U.S. orthodontists are members of the AAO) indicated that 1,358,000 patients began orthodontic treatment in 1992. The mean cost of orthodontic treatment is estimated to be $3200 per child patient in the permanent dentition and $3500 per adult patient. Approximately, 77% of the new patients started in 1992 were under the age of 18. Few orthodontists would disagree that patient nonadherence is a challenging problem. In addition to its economic cost, nonadherence can result in protracted treatment and failure to achieve orthodontic correction. Complicating the task of the orthodontist is a lack of objective information about the degree to which patients are actually complying with the prescribed regimen (e.g., headgear use). One recent survey of orthodontists found that 80% of the respondents said that they had no particular method for assessing adherence.

In broad terms, orthodontic treatment goals are to provide patients with properly aligned teeth, a functional occlusion, and optimal facial aesthetics. An Angle Class II malocclusion occurs in 15 to 20% of U.S. children. This common condition occurs in both genders, is not related to socioeconomic status, and is rarely self-correcting. This type of malocclusion is diagnosed in the antero-posterior plane of space as a discrepancy between the positioning of the maxillary and mandibular dentitions. Specifically, the mandibular dentition is located more posteriorly than would be ideal relative to the maxillary dentition. Patients with this malocclusion (Angle Class II, division I) are typically described as having proclined or protrusive upper incisors, a retrusive lower jaw, and excess overjet. In all but the mild Class II patients, an underlying skeletal disharmony is present and is at least partially responsible for the spatial malrelations between the teeth. Consequently, a common treatment for this malocclusion involves the application of orthopedic forces in growing children to alter the relative growth pattern between the jaws, thus bringing them into proper alignment. This is most commonly accomplished by means of a headgear appliance which restrains the forward growth of the maxilla while allowing the forward growth of the mandible to continue unimpeded. A recent national survey reported that nine out of ten orthodontists use headgear appliances "routinely" or "occasionally" in the treatment of Class II malocclusions.

Orthodontic treatment frequently relies on the use of removable appliances to provide forces to teeth and bones in order to correct spatial malrelations between the teeth and/or jawbones. The removable nature of these appliances requires that patients (typically growing children) comply with the orthodontist's request to wear the device. Unfortunately, poor compliance is the rule rather than the exception with wearing removable orthodontic appliances. This generic problem is also pervasive in medicine (e.g., taking medications as prescribed).

Headgear appliances have been used since the nineteenth century. They are a removable type of orthodontic appliance that patients are typically advised to wear for 12–14 hours a day. A headgear consists of an inner metal bow that enters the mouth and attaches to the upper jaw by means of the maxillary first molars. Two arms extend from this inner bow to the outside of the mouth and then curve back along the outside of the cheeks and point toward the back of the head. A soft pliable cloth strap is placed on the back of the neck and a force module is connected at each end of the neck strap to the respective outer arm of the metal headgear bow. Thus, the back of the neck supplies the extraoral anchorage for the force modules to provide a posteriorly pulling force on the upper jaw. This force inhibits forward growth of the upper jaw relative to the normally growing lower jaw. The differential growth between the jaws corrects the patient's orthodontic problem. If this type of problem is not corrected in a growing child (when growth alteration is possible), then treatment options become limited to the extraction of teeth or the surgical repositioning of the patient's jaws. In addition to the orthopedic correction of the jaw relationship, headgear appliances also correct the malocclusion by means of dentoalveolar changes.

In 1974, Northcutt described the first timing headgear, a device that was developed and marketed by the Aledyne Corporation. Northcutt anecdotally reported that after introducing the timing headgear, his patients increased wearing their headgear from an average of 35–50 hours per week to over 100 hours per week. Unfortunately this was not an experiment but simply an anecdotal observation. However, a recent study had 14 subjects monitor their headgear wear using a calendar while actual headgear wear data were collected from a covert "homebrew" headgear timer. Simple monitoring resulted in large (p<0.05) increases in compliance. Additional evidence indicates that providing feedback to make the monitoring of adherent behavior possible has a significant beneficial effect on compliance. Proper design of a headgear monitor could make monitoring very easy and would also permit the application of sophisticated behavior modification principles to increase headgear wear since the behavior could now be effectively monitored and consequently, reinforced.

There were several deficiencies in the Aledyne type of headgear timer and consequently, it is no longer in production. The worst deficiency was that in an in vitro reliability test, 9 out of 14 timers were more than 70% inaccurate. The design of the timer also had other flaws. The wear time could only be decoded by connecting the headgear to a costly digital readout meter in the orthodontist's office. Thus, patients and their parents could not monitor wear time between orthodontic appointments. In addition, the timer could only be used with a specific manufacturer's headgear design and force module. To the best of our knowledge, there are no commercial companies currently manufacturing headgear timers. As a consequence, a recent article described a way to make a "homebrew" timer from a wristwatch but, like the previous model, it required 1) attaching the elastic module to the neck strap, thus removing the orthodontist's option of changing or selecting a different elastic module without disassembling the unit and 2) disabling the safety disconnect feature of the force module (which is a required part of all headgear appliances). In addition, this simple timer can be easily deceived by the patient which is a significant limitation when attempting to determine an accurate measure of patient compliance. As a consequence of our novel approach to the problem, we have designed and constructed a prototype headgear monitor (based upon scientific principles of orthodontics, behavioral science and electrical engineering) that corrects the flaws of previous headgear timers. Data from the National Health Survey (1973) indicates that 15–20% of U.S. children have the type of malocclusion (Angle Class II malocclusion) that is commonly treated using a headgear appliance. A reliable compliance monitor capable of measuring the duration and magnitude of applied forces would be an invaluable research tool to enhance our treatment of this condition. Furthermore, if headgear monitoring was shown to improve orthodontic treatment outcomes, it could become a standard component of headgear appliances.

SUMMARY OF THE INVENTION

The present invention provides a compliance monitor for orthodontic headgear of the type comprising a linear spring-force module. The module includes first and second opposite attachment members interconnected to provide spring tension when moved linearly apart. A position sensor is positioned on the module to detect linear movement between the attachment members. Also on board is a processor means, such as a battery-operated microprocessor, for receiving a signal from the position sensor and determining whether the detected movement is sufficiently variable to be biological in origin. A memory means, such as a non-volatile EEPROM, records the determination made by the processor means.

In preferred form, a visual display will indicate the recorded determinations and provide a cumulative record of compliance. Also in preferred form, the position sensor includes a magnet attached to move with one of the attachment members and at least one Hall effect sensor positioned to sense linear movement of the magnet. By using a plurality of Hall effect sensors, movement and position of the magnet can be unambiguously determined. Thus, the device can be calibrated to provide a quantitative measurement of spring tension being applied over time.

According to another aspect of the invention, an optical interface, such as an infrared LED/photo transistor may be used to download recorded data and to upload programming commands.

The present invention also includes the method of measuring and motivating orthodontic headgear compliance. A linear spring-force module and a position sensor for detecting linear movement in the module are provided. Signals are received from the sensor and processed to determine whether the detected movement is sufficiently variable to be biological in origin. Multiple determinations are recorded over time for evaluation of headgear wear compliance.

By visually displaying the recorded determinations in cumulative record, the user can be motivated into further compliance. Additionally, quantitative measurement of spring tension applied can be used in therapeutic valuation.

The present invention is intended to both measure compliance and cause a substantial increase in patience compliance. The device may be sufficiently miniaturized to be incorporated into existing orthodontic removable appliances and will give precise records of patient compliance. A notable benefit is this invention's ability to screen out false or faked data using a software algorithm. Prolonged static tension on the force module will not be recorded as compliance. The movements and tension measured must be sufficiently variable to be considered biological in origin. Feedback on compliance is readily available to patients, parents, and the orthodontist and, if desired, the actual data can be downloaded to computer equipment commonly found in orthodontic offices.

Because of the large potential market, previous commercial attempts have been made to develop devices to assess orthodontic compliance. The device we have designed has overcome the problems with previous designs. In addition, psychological principles have been incorporated into our design such that this model (as opposed to previous attempts) may improve compliance and consequently treatment outcomes.

BRIEF DESCRIPTION OF THE DRAWINGS

Like reference numerals are used to represent like parts throughout the various figures of the drawing, wherein:

FIG. 1 is a pictorial view showing a patient wearing orthodontic headgear which employs a pair of safety-release mechanisms in which the present use monitoring device has been incorporated according to the present invention;

FIG. 2 is an enlarged fragmentary side elevation illustrating details of construction of one of the safety-release mechanisms used in the headgear which incorporates the present invention;

FIG. 3 is a view taken from the top side of FIG. 2;

FIG. 4 is a cross-sectional view taken substantially along line 4—4 of FIG. 2;

FIG. 8 is a side view of an attachment strap showing an overlay relative position of the sensor components when the spring is in a relaxed position;

FIG. 9 is a side schematic view showing relative placement of components in the present invention.

BEST MODE FOR CARRYING OUT THE INVENTION

Figure 5:
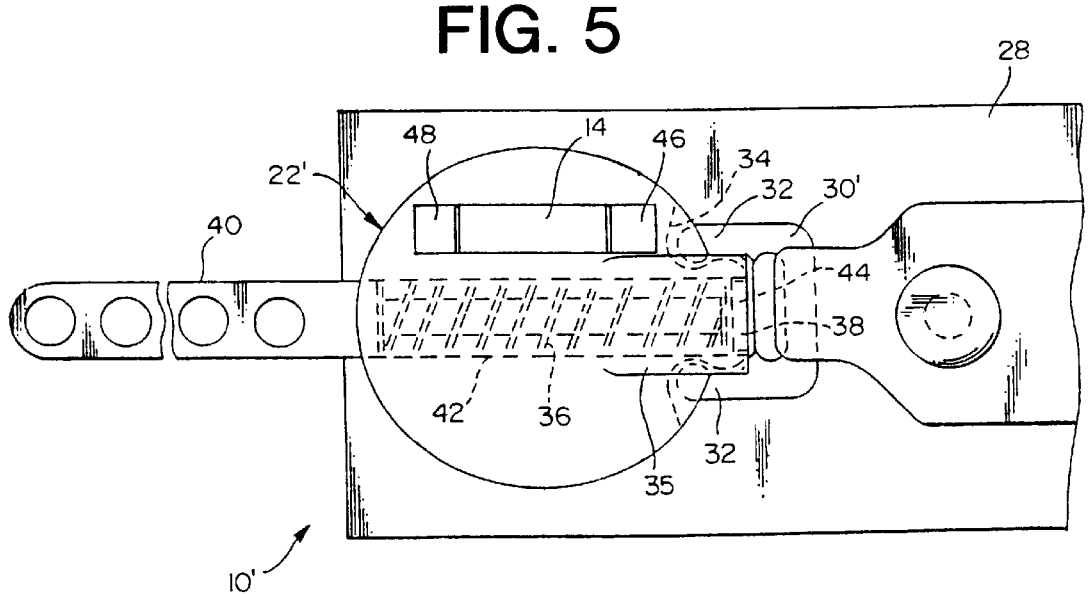
FIG. 5 is an enlarged fragmentary side elevation illustrating details of an alternate preferred construction of one of the safety-release mechanisms used in the headgear which incorporates the present invention.

Briefly, our device 10 uses a low-energy consumption, battery-powered microprocessor 12 with liquid crystal display (LCD) 14 to provide compliance feedback to the patient, parent, and orthodontist. The microprocessor uses two types of magnetic sensing devices 16, 18, 19 (as well as a software routine to prevent patient deception) to measure adherence. Headgear use is logged into non-volatile memory (EEPROM) 20. Downloading of the data is available using commonly available personal computers (e.g., IBM and Macintosh) for tabular or graphic display and medical records.

Referring particularly to FIG. 1, an orthodontic headgear 24 is shown properly positioned for use on a patient's head. Headgear 24 includes a conventional facebow 26 with outer ends extending along the opposite sides of the patient's face, and a conventional flexible non-elastic neck strap 28. Indicated generally at 22, are two identical safety-release tension-applying mechanisms which apply rearwardly-directed spring tension to the facebow 26 in a conventional manner.

Referring also to FIGS. 2–4, a safety-release mechanism comprises an open-ended snap ring 30 attached to the neck strap 28 with a pair of free end portions 32 which engage a groove 34 of a force-applying module 22. In the event that the facebow 26 is pulled forwardly away from the wearer's face, the amount of tension transmitted through the safety release mechanisms reaches the maximum tension level which they are capable of transmitting, and on this occurring, one or both of the mechanisms release the connection between the facebow 26 and the neck strap 28, so that no slingshot effect can occur. The amount of force necessary to disengage the safety-release mechanism is determined by the force necessary to spread the free end portions 32 a sufficient distance to allow them to slide outwardly through the groove 34.

Figure 6:
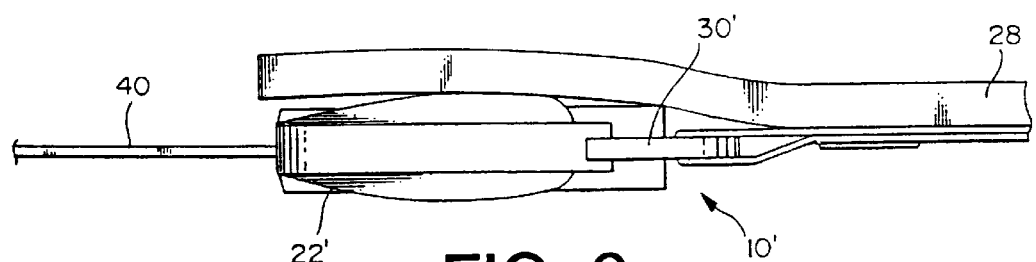
FIG. 6 is a view taken from the top side of FIG. 5.

FIGS. 5 and 6 show an alternate preferred embodiment of the device 10'. This embodiment 10' functions virtually identically to that described above, but provides more usable internal space for housing electronic components without increasing the overall size of the unit 10'. Space efficiency is achieved by using an alternate open-ended snap ring 30' which is smaller in overall size and engages a groove 34 which is part of a rearwardly-extending portion 35.

Spring tension is applied to the facebow 26 by an internal spring 36 within the force module 22, 22'. This spring 36 is partially compressed by a head portion 38 of the connection strap 40 that compresses the spring 36 while the headgear 24 is in use. Because the spring 36 is not fully compressed, slight movement is permitted without significant restriction in order to allow the wearer to freely rotate his or her head. A thorough disclosure of a typical connector device may be found in U.S. Pat. No. 4,226,589, the contents of which is incorporated herein by specific reference.

Several insights enabled the development of this technology. First was the realization that the active therapeutic ingredient of headgear treatment is the force which is generated entirely within the "force module" 22 and which is then transferred to the upper jaw by means of a static metal facebow 26. Measuring some aspect of the force generation process would be an ideal way to assess use of the headgear (i.e., compliance). Second was the idea that this measurement should occur entirely within the "force module" 22 (i.e., where the force is generated) and thus be independent of the type of facebow 26 or neck strap 28 that the orthodontist employs. This aspect of the design is compatible with the safety disconnect feature of the force module from the neck strap that is important in headgear design.

Upon examination of a typical orthodontic force module 22, one finds a passive coil spring 38 resting in a hollow cylindrically shaped hole 42 in the center of the force module. The force is generated by compressing that spring within the force module. When the headgear is properly worn, the spring is held in a compressed (active) position by attaching one end of the force module to the neck strap 28 and the other component of the force module (i.e., the one that moves and compresses the spring) to the outer arm of the facebow. The patient is instructed to attach the adjustable portion 40 of the force module 22 to the outer arm of the facebow 26 so that force is generated (i.e., the spring is being compressed). In this position, the spring can only become more relaxed if the outer arm of the facebow 26 moves closer to the back of the head. This indeed does occur during natural changes in head position made by the patient. As the head turns or moves, the springs in the right and left force modules 22 can relax or become more compressed. This provides another crucial component to the design of our monitor 10. Most attempts to deceive a headgear timer would involve compressing the spring. Most simply, this could be accomplished by placing the headgear on an inanimate mannequin head or by holding the spring 36 in an active position by putting weights (e.g., a stack of books) on either side of the force module 22. However, these attempts at deception compress the spring in a static manner whereas during actual wear by a patient, the springs 36 are continually adjusting to changes in head position. Thus, if the degree of spring compression is assessed over time, a software algorithm can be used to distinguish static (invalid) wear from the variable degree of spring compression that occurs during actual (valid) headgear wear. The specifics of the algorithm (based on some statistical measure of signal variability) as well as when and for what duration the signal is sampled can be determined from data collected from patients wearing the device. Using well-known statistical equations, the collected data may be filtered with a median filter to remove spikes created by extraneous noise. Based on the data collected from valid headgear wear and invalid static or mechanically-produced movement having a regularity that indicates attempted deception, the standard deviation and variance of the signal is evaluated over a predetermined period of time. Using these criteria, it is believed that a person of ordinary skill could easily write an appropriate software program for use with the present invention.

Finally, the last crucial factor in our new design for a headgear monitor is the ability to sense the degree of compression of the spring within the force module, 22, 22'. The back of the spring 36 is brought closer to front of the force module during compression. The patient pulls the movable portion 40 of the force module 22, 22' (with the spring) forward to attach it to the outer arm of the facebow 26. This movable portion of the force module 22, 22' has a "stop" 38 that does not allow the spring 36 to remain passive within the module but forces it to compress as the subject pulls that moveable part 40 of the force module forward to the outer arm of the facebow 26. Thus, the stop 38 has changed its position within the force module 22, 22' and the spring 36 is being compressed.

A powerful magnet 44 is attached to the stop 38. Two spatially-fixed Hall sensors 18, 19 in the outer part of the force module 22 can unambiguously measure the relative change in magnetic strength as the magnet 44 moves within the force module 22. A Hall sensor measures the change in magnetic field strength. Thus, the Hall sensors 18, 19 provide an analog measure of magnetic field strength that relates directly to the position of the stop 38 and thus the amount of spring compression. A small magnetic reed switch 16 can also be employed to initially sense the position of the magnet 44 when the headgear is first put on and thus eliminate the need to continuously use the Hall sensor 18 to track magnet position which would consume more power.

A TSS 400-S3 microprocessor 12 from Texas Instruments can monitor the magnetic reed switch 16, and the analog signal from the Hall sensors 18, 19. It can evaluate the Hall signal statistically for evidence of actual wear by assessing the variability in the signal. Actual wear time can be measured and displayed on a LCD 14 using the microprocessor 12. Data can be saved in non-volatile memory 20 using EEPROM. The microprocessor 12 can also detect infrared pulses sent from an external unit (not shown) to the infrared photo-transistor 47 which signals the microprocessor 12 to do a variety of functions such as reset the display, set the clock, reload new software routines, or download the data via an infrared LED 46 that is included as part of the headgear monitor.

The TSS 400-S3 sensor signal processor 12 includes time-keeping capability, a 12-bit multi-channel analog-to-digital conversion, an LCD driver, 6 digital outputs, a 4-bit input port, and is easily programmable. This microprocessor is available as a die which facilitates ultra-miniaturization for use in the commercial product. The sensors used are a magnetic reed switch 16 that can detect when force is first applied to the headgear. Two Hall sensors 18, 19 unambiguously measure the spring position that generates the headgear forces. Thus, relative force may be quantitatively measured and recorded.

The four-digit LCD 14 can be directly driven by the microprocessor 12 and can alternately display the average hours of wear per day, as well as the cumulative number of hours worn since last reset. All electronics may be sealed for protection against water and tampering.

The commonly-available three-volt lithium battery power source 48 will provide adequate power for normal use of the electronics described above. The microprocessor is optimized for lithium battery power and consumes as little as 80 microamps in the active mode, and as little as 4 microamps in the sleep mode. The memory is non-volatile and data will not be lost due to power loss.

Figure 7:
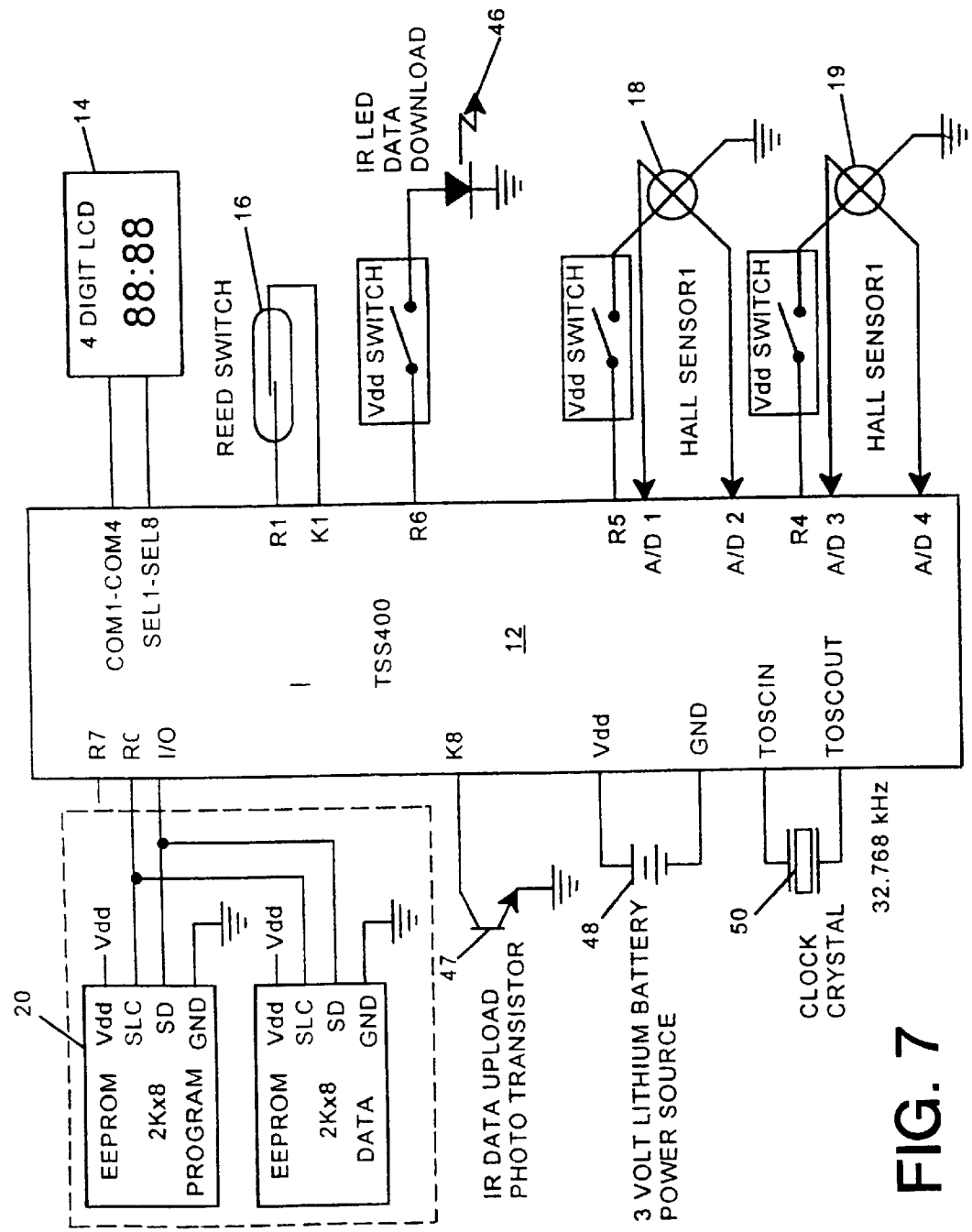
FIG. 7 is an electrical circuit schematic of the present invention.

By incorporating an infrared LED 46 and photo transistor 47 into the force module 22, 22', bi-directional communication between the module and an office computer can be achieved via an external serial interface. Thus, headgear use data can be easily downloaded and programming, including clearing the datalog and changing software protocols, can be accomplished using the infrared upload feature. Timing may be controlled by a typical quartz clock device 50. The entire electronic circuitry is shown schematically in FIG. 7.

It is preferred that the magnet 44 be shaped and oriented so as to optimize sensitivity of the Hall sensor 18. As shown schematically in FIG. 8, when moving from the relaxed to active spring position, the magnet moves over a range 52 whereby it initially changes the state of the reed switch 16 and then the increasing magnetic field strength can be sensed by the Hall sensors 18, 19. If desired, a rare earth magnet having a proportionally greater magnetic field strength relative to its size may be used in the device.

FIG. 9 schematically shows the preferred arrangement of components within the force module 22. The specific arrangement is not critical to this invention, however, it is important that each of the components be sufficiently miniaturized so as not to significantly increase the size or mass of the force module 22, 22'.

If desired, the present invention may be adapted to record the magnetic field strength recorded by the Hall sensors 18, 19 in order to correct data with respect to not only the amount of time the headgear 24 was in use, but also to quantitate the amount of force applied during a specified time interval.

Figure 10:
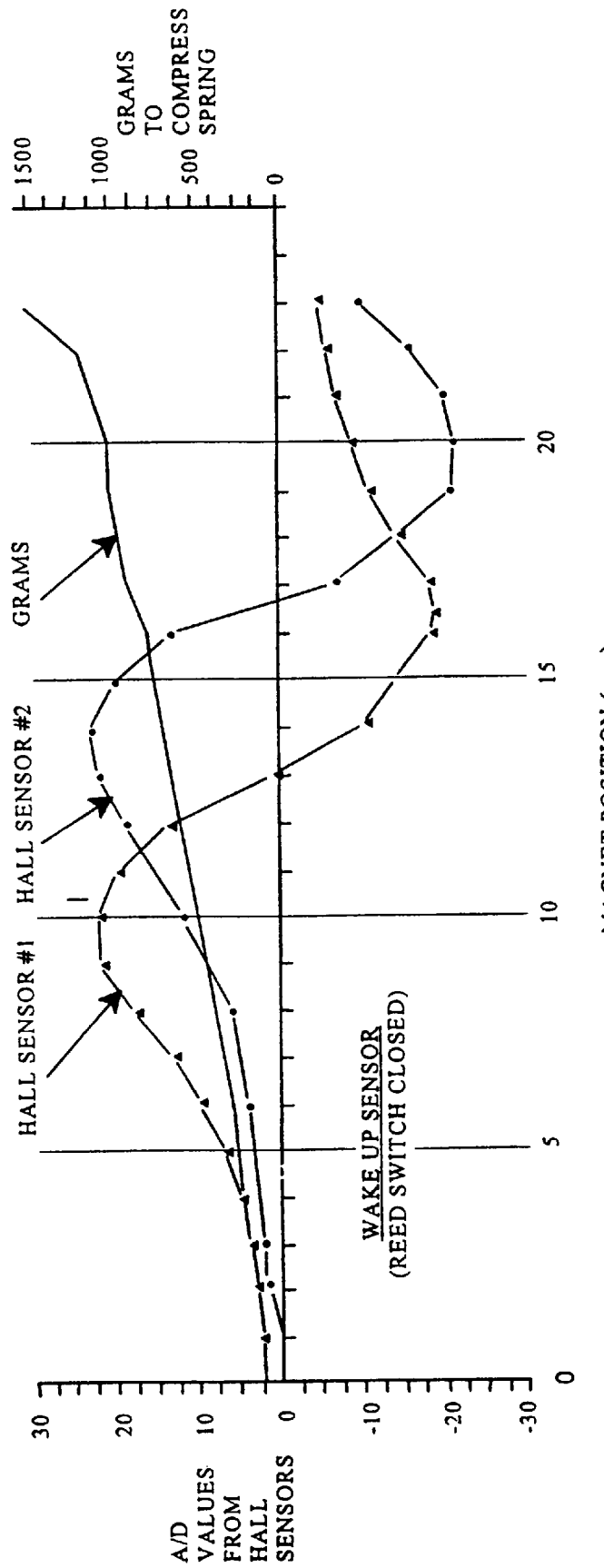
FIG. 10 is a graph showing relative A/D values from linearly-spaced Hall sensors as compared to applied spring force in grams.

Referring to FIG. 10, therein is shown a graph based upon laboratory data showing analog-to-digital values of the linearly spaced-apart Hall sensors 18, 19. The active zone of a wake-up sensor, such as reed switch 16, is also shown. As the magnet 44 is moved along its path of travel, the value recorded by each Hall sensor first rises and then drops. A single Hall sensor is sufficient to determine compliance qualitatively. If it is desired to quantitatively measure and record the amount of force being applied over a given period of time, it is necessary to have more than one Hall sensor. This is because more than one linear magnet position could be associated with a given positive or negative value measured by a single Hall sensor. This creates a degree of ambiguity. A straightforward way to remove this ambiguity is to use a plurality of Hall sensors, linearly spaced apart so that, as shown in FIG. 10, the magnet position can be determined without ambiguity. By calibration of the unit, a relative or exact quantity of force may be associated with any magnet position. In preferred form, the microprocessor 12 would sample first one, then the other Hall sensor 18, 19 close in time.

The processor 12 provides this solution to an engineering difficulty commonly associated with the use of Hall sensors. Two inputs of the high impedance 12-bit analog-to-digital (A/D) of the processor are connected to each of the differential voltage leads of the Hall devices. The A/D values from each lead of a single Hall sensor are sampled and the numeric difference is used as the sensed value of the magnetic field. Because the TSS-400 microprocessor has four A/D inputs, a plurality of Hall sensors can be connected without additional electronics. The differential signal removes the effect of Hall voltage drift in relation to the power supply reference due to temperature and supply changes. The high impedance inputs provide the required independence of the sensing voltage to the Hall current supply. The 12-bit A/D resolution can sense 150 microvolt changes, thereby eliminating the need for a separate operational amplifier.

As discussed above, it is important that the headgear monitor of the present invention discriminate between actual compliance and attempted mimicking. This distinction may be determined by the processor 12 utilizing appropriate software designed to log the headgear wear time while identifying the deceptive attempts at mimicking headgear use (i.e., cheating). The software must also optimize energy use to prolong battery life.

The processor is put into low power use (i.e., sleep mode) until the magnetic reed switch is activated when the headgear is put on the head. The processor is then activated and the program tentatively records the wear start time. By sensing the spring position with the Hall sensors 18, 19, the program periodically compares the present position with previous measurements. Due to the biological variability or randomness of spring position during normal headgear use, a software algorithm can determine true wear time as opposed to a prolonged static spring position that would be suggestive of attempted mimicking.

The program can power down the processor at predetermined time intervals and reactivate it to perform repeated assessments of spring position (i.e., validation of wear time). Sampling need only be performed every few minutes because more precise measurement of wear time may be unnecessary. This also helps to optimize energy use and prolong battery life. When the spring is relaxed to a passive position, the tentative stop time is recorded. If no activity indicating wear is sensed in a nominal period (e.g., thirty minutes), the validated and time-stamped wear data (e.g., on and off time, mean spring position) are logged into the nonvolatile memory 20. Average force values may be obtained using a look-up table derived from previous calibration of the spring position versus force relationship. Associated software of well-known variety will allow bi-directional communication between the compliance monitor and a computer to both download data from the monitor, as well as to reset and revise software in the monitor. Additionally, associated software may allow the evaluation of headgear monitor data in both tabular and graphical forms.

Although the use of Hall sensors and magnet is the preferred manner for detecting movements, a variety of equivalent alternative options may be employed. For example, a device creating and measuring variable resistance either by mechanical or other means may be used. Also, an optically-coded position sensor or fluid pressure sensor may be substituted. Other possible sensors include ultrasonic devices, magneto-resistive sensors or material that can act as a compressible variable force transducer. Any means for sensing spring position and/or compression that may be sufficiently miniaturized may perform equivalently.

Many other variations and modifications may be made to the present invention without departing from its spirit and scope. Patent protection is not to be defined by the presently-disclosed preferred embodiment, but rather by the following claim or claims interpreted according to accepted doctrines of claim interpretation including the doctrine of equivalents and reversal of parts.

What is claimed is:

1. A compliance monitor for orthodontic headgear of the type applying linear spring-force, said compliance monitor comprising:

a linear spring-force module having first and second opposite attachment members interconnected so as to provide spring tension when moved linearly apart from one another;

a position sensor positioned in the module to detect linear movement between said attachment members;

processor means for receiving a signal from said position sensor and determining whether such movement over a predetermined time period is sufficiently varying to be the result of human movement; and memory means for recording determination made by said processor means.

2. The compliance monitor of claim 1, further comprising a visual display for indicating the recorded determinations made by the processor means.

3. The compliance monitor of claim 2, wherein said memory means also provides a cumulative record of determinations made by said processor means.

4. The compliance monitor of claim 1, wherein said position sensor includes a magnet attached to move with one of said attachment members and a Hall effect sensor positioned to sense linear movement of said magnet.

5. The compliance monitor of claim 4, comprising a plurality of Hall effect sensor positioned on the spring-force module along the path of said magnet for unambiguously sensing movement and position of said magnet.

6. The compliance monitor of claim 1, comprising a plurality of linear position sensors positioned to quantify linear movement and relative position between said attachment members.

7. The compliance monitor of claim 1, wherein said position sensor provides a quantitative measurement of spring tension applied between said first and second opposite attachment members.

8. The compliance monitor of claim 7, further comprising a magnet attached to move with one of said first and second attachment members and said linear position sensor comprises a plurality of Hall effect sensors to unambiguously detect and quantify linear movement between said attachment members.

9. The compliance monitor of claim 1, further comprising a means for transferring said recorded determinations from the memory means to an external device.

10. The compliance monitor of claim 9, wherein said transferring means includes an optical interface.

11. The compliance monitor of claim 9, further comprising a means for transferring programming information from an external device to said processor means.

12. A method of measuring and motivating orthodontic headgear compliance, comprising:

providing a linear spring-force applying module;

providing a position sensor for detecting linear movement in said spring-force module;

processing signals received from said sensor and determining whether such movement is sufficiently variable to be biological in origin and recording such signals as indicating an in-use mode; and recording multiple determinations over time for evaluation of headgear wear compliance by measurement of cumulative time in said in-use mode.

13. The method of claim 12, further comprising the step of visually displaying the recorded determinations made by the processor.

14. The method of claim 13, wherein a cumulative record of compliance is recorded.

15. The method of claim 12, wherein said position sensor includes a magnet attached to move with one of said attachment members and a Hall effect sensor positioned to sense linear movement of said magnet.

16. The method of claim 15, wherein movement and position of said magnet is unambiguously sensed by a plurality of Hall effect sensors.

17. The method of claim 12, wherein a plurality of position sensors are positioned to detect linear movement and position of said spring-force module.

18. The method of claim 12, further comprising the step of providing a quantitative measurement of spring force.

19. The method of claim 12, further comprising the step of transferring said recorded determinations from the memory means to an external device.

20. The method of claim 19, wherein said transferring is accomplished by an optical interface.

* * * * *